United States Patent
Typpo

[19]

[11] Patent Number: 6,031,620

[45] Date of Patent: Feb. 29, 2000

[54] GLOSS SENSOR RESISTANT TO TILTING AND SHIFTING PAPER AND WITH IMPROVED CALIBRATION

[75] Inventor: Pekka M. Typpo, Cupertino, Calif.

[73] Assignee: Impact Systems, Inc., Los Gatos, Calif.

[21] Appl. No.: 09/066,828

[22] Filed: Apr. 28, 1998

Related U.S. Application Data

[63] Continuation-in-part of application No. 08/846,897, May 1, 1997, abandoned.

[51] Int. Cl.⁷ ............................. G01N 21/55; G01B 11/30
[52] U.S. Cl. ............................................ 356/445; 356/371
[58] Field of Search ...................................... 356/445, 446, 356/371, 429, 448

[56] References Cited

U.S. PATENT DOCUMENTS

| | | | |
|---|---|---|---|
| 3,636,361 | 1/1972 | Bowers | 356/448 |
| 3,890,049 | 6/1975 | Collins et al. | 356/209 |
| 3,999,864 | 12/1976 | Mutter | 356/448 |
| 4,139,307 | 2/1979 | Clarke | 356/446 |
| 4,989,984 | 2/1991 | Salinger | 356/445 |
| 5,054,930 | 10/1991 | Adelson | 356/429 |
| 5,146,097 | 9/1992 | Fujiwara et al. | 356/446 |
| 5,550,632 | 8/1996 | Harata | 356/446 |
| 5,570,183 | 10/1996 | Wiles | 356/371 |

*Primary Examiner*—Frank G. Font
*Assistant Examiner*—Zandra V. Smith
*Attorney, Agent, or Firm*—Flehr Hohbach Test Albritton & Herbert LLP

[57] ABSTRACT

A gloss sensor for determining the gloss of a surface, for example, of moving paper being produced by a paper making machine. The gloss sensor normally is installed in a scanner which scans the moving paper in a crosswise direction. It includes a standard TAPPI light source which impinges upon the paper at a specified angle and the intensity of the detected reflected light is related to gloss. Calibration is provided by an oscillating angle light source which with the same lamp has a direct reference path to the detector. Compensation for tilting or shifting paper is provided by the same oscillating light source which when the paper tilts or shifts still allows a reflected light beam to reach the detector. Change of angle from the standard TAPPI angle due to parallel paper shifts is compensated.

14 Claims, 7 Drawing Sheets

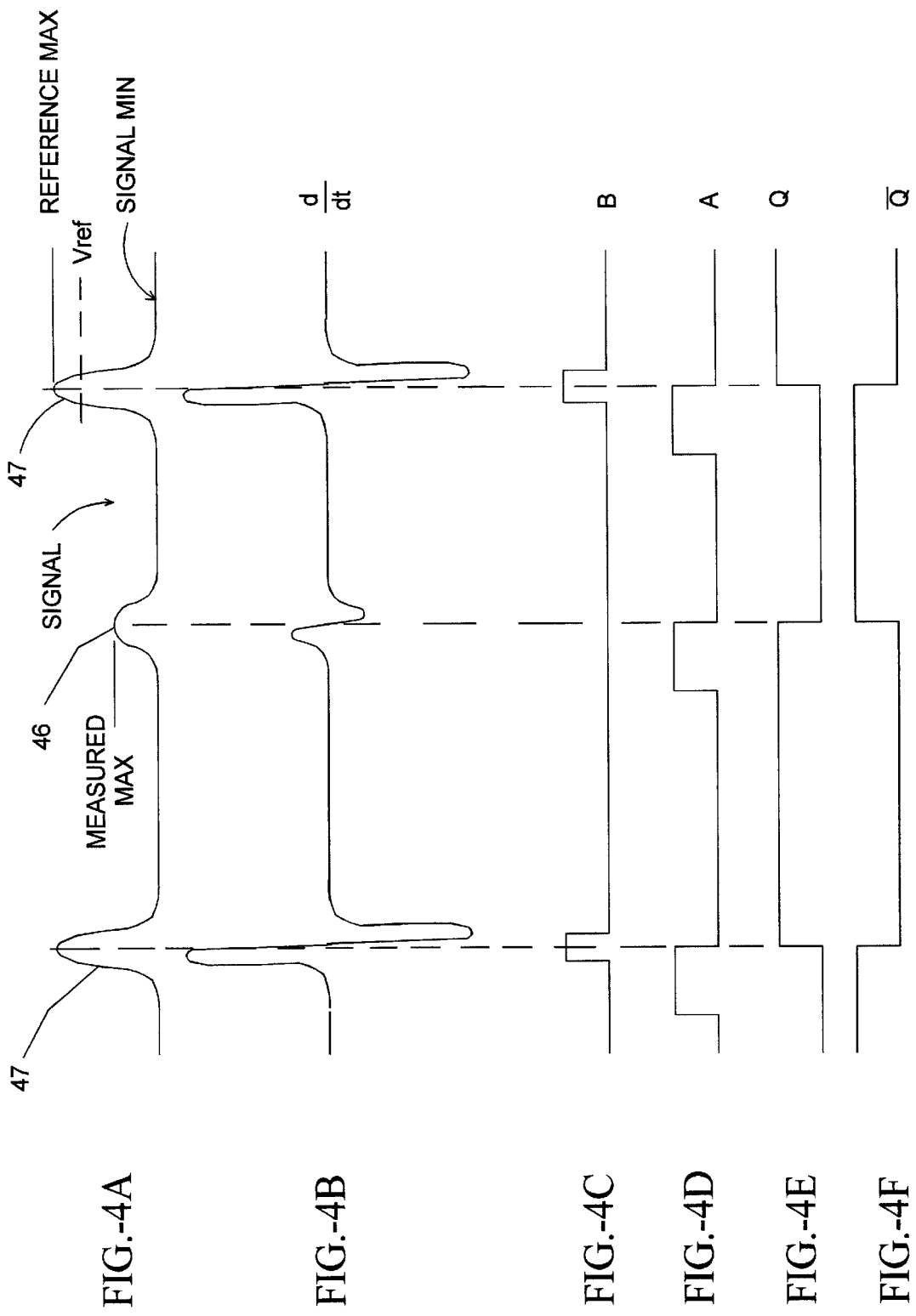

6,031,620

GLOSS SENSOR RESISTANT TO TILTING AND SHIFTING PAPER AND WITH IMPROVED CALIBRATION

RELATED APPLICATIONS

This application is a continuation-in-part of application Ser. No. 08/846,897 filed May 1, 1997, now abandoned.

The present invention is directed to a gloss sensor resistant to tilting and shifting paper and with improved calibration and more specifically to a sensor for use with a paper making machine.

BACKGROUND OF THE INVENTION

In the paper making industry where paper is being produced at a high rate from a paper making machine, for quality and feedback control the paper is scanned crosswise by a moving head containing a number of sensors to determine parameters such as basis weight, moisture and gloss. The final value of gloss is a rather arbitrary number determined by standards in the paper making industry; namely, TAPPI standard T 480 om-90 which involves projecting onto the paper surface an incident beam of light at a particular angle (for example, 15°), detecting the reflected beam and measuring its intensity. To calibrate the above TAPPI standard a polished black glass standard is used. Then an intermediate standard which is calibrated against that may be a polished ceramic tile. Some gloss sensors actually mechanically carry such a tile in a moving measuring head and lower the tile into the light beam to calibrate the instrument. This, of course, is mechanically complicated and there are some problems of environmental conditions such as heat, dirt and also accurate positioning.

Another gloss technique of Valmet Automation of Canada provides a separate reference beam apart from the incident measuring beam. Here there are two separate light sources and detectors; moreover, the light source is a different type than the standard source defined by the above TAPPI standards. Thus, the correlation to the industry standard is suspect.

Finally the moving paper sheet inherently tilts or produces waves so that the surface moves to, in some cases, during the measuring process cause the reflected beam to miss the detector entirely. Also there are parallel shifts.

All of the foregoing implies a reliability of gloss measurement much less than desired.

OBJECT AND SUMMARY OF THE INVENTION

It is therefore an object of the present invention to provide an improved gloss sensor.

In accordance with the above object there is provided a gloss sensor for determining the gloss of a surface comprising a light source for emitting an incident light beam onto the surface at an angle causing the light beam to be reflected from the surface. A light detector is positioned to detect the reflected light. In one aspect of the invention the light source includes a single lamp and means for aiming both the incident light beam onto the surface and also a reference light beam aimed directly at the detector without reflection. The light source provides an emission of light at oscillating angles substantially near the incident angle whereby any tilt or shift of the moving surface which would otherwise cause the reflected light to miss the detector is compensated for. The magnitude of the detected reflected light is sensed to determine the gloss and the reference beam is used for calibration purposes. Any error in the gloss value due to a parallel shift of the paper is compensated.

BRIEF DESCRIPTION OF THE DRAWINGS

FIGS. 4A through 4F are waveforms useful in understanding the invention.

DETAILED DESCRIPTION OF THE PREFERRED EMBODIMENTS

Figure 1:
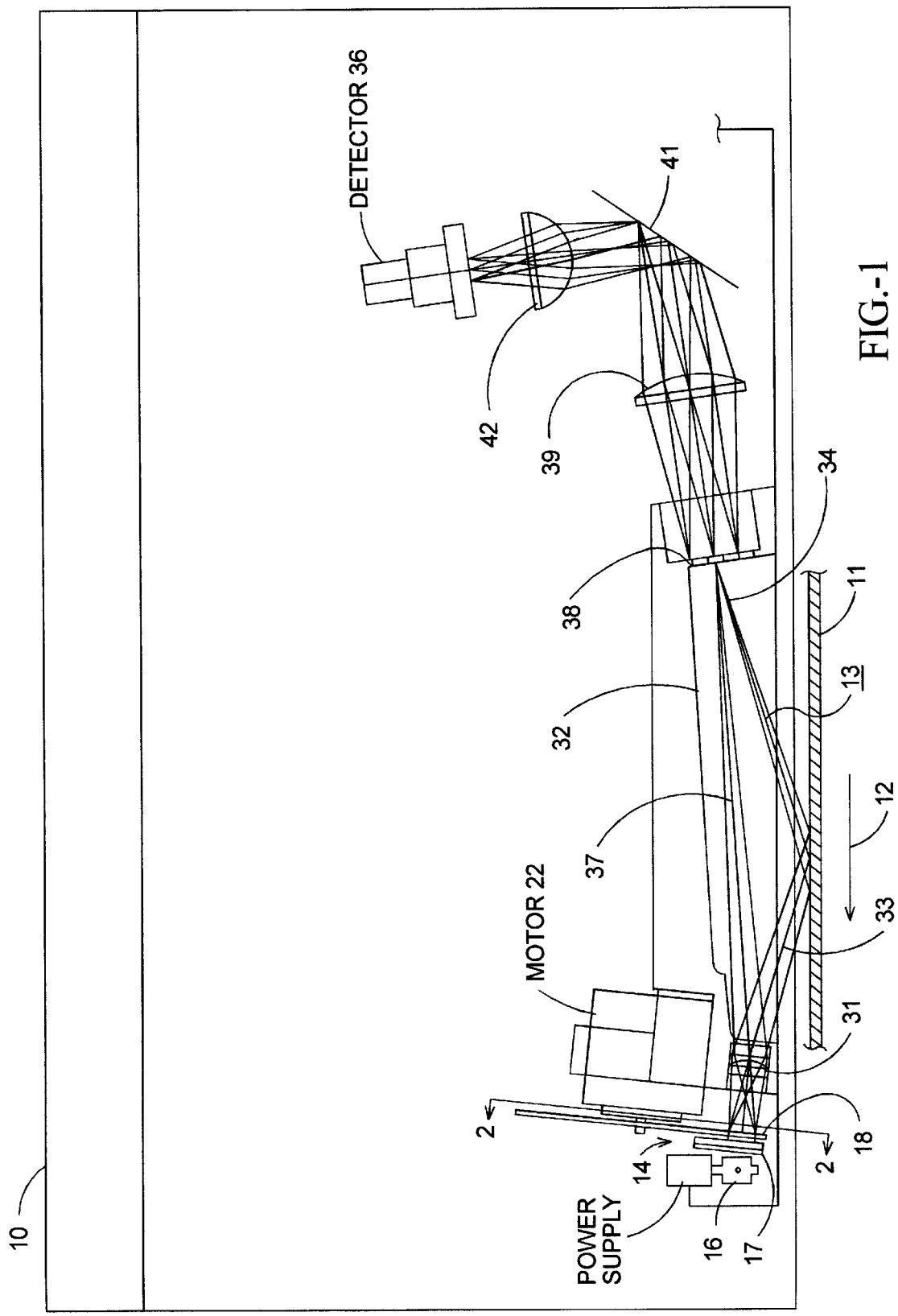
FIG. 1 is a cross sectional view of a gloss sensor as it would be mounted in a scanning head of a paper making machine.

FIG. 1 illustrates a scanning sensor head 10 as it would scan a moving paper sheet 11, moving in the machine direction 12, crosswise to that direction (into or out of the drawing as illustrated in FIG. 1). The various light beams 13 illustrated incident on the paper surface of paper 11 and reflected from it represent one slice of the paper 11. Eventually as the sensor unit 10 moves across the paper, hundreds of samples would be taken of the gloss parameter for a single crosswise scan Measuring head 10 as discussed above might include other measuring devices such as for basic weight and moisture. However only the gloss sensor is shown and includes an overall light source 14 which has a lamp 16 which is a standard lamp which under TAPPI standards has a color temperature of 2850° K. which is juxtaposed with a diffuser sheet 17 and a rectangular vertical window 18. Sheet 17 has a thickness of 20–30 microns and is composed of a tetrafluoroethylene resin; e.g. Teflon™.

Figure 3:
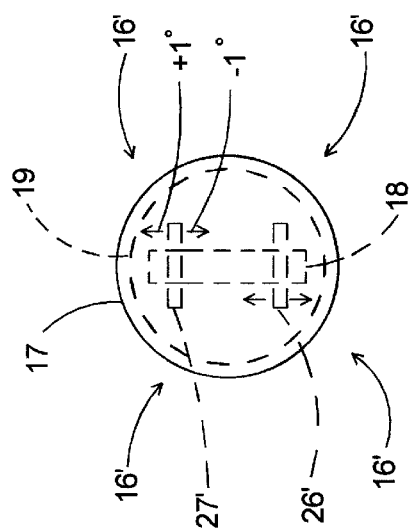
FIG. 3 is a simplified plan view of another portion of FIG. 1 which is in effect juxtaposed with FIG. 2.

Referring to FIG. 3 the diffuser sheet is shown at 17 and then behind it is a metal sheet or coating 19 having the vertical window 18. And the rays of the lamp 16 shining on the face of the diffuser sheet are shown as the rays 16'.

Figure 2:
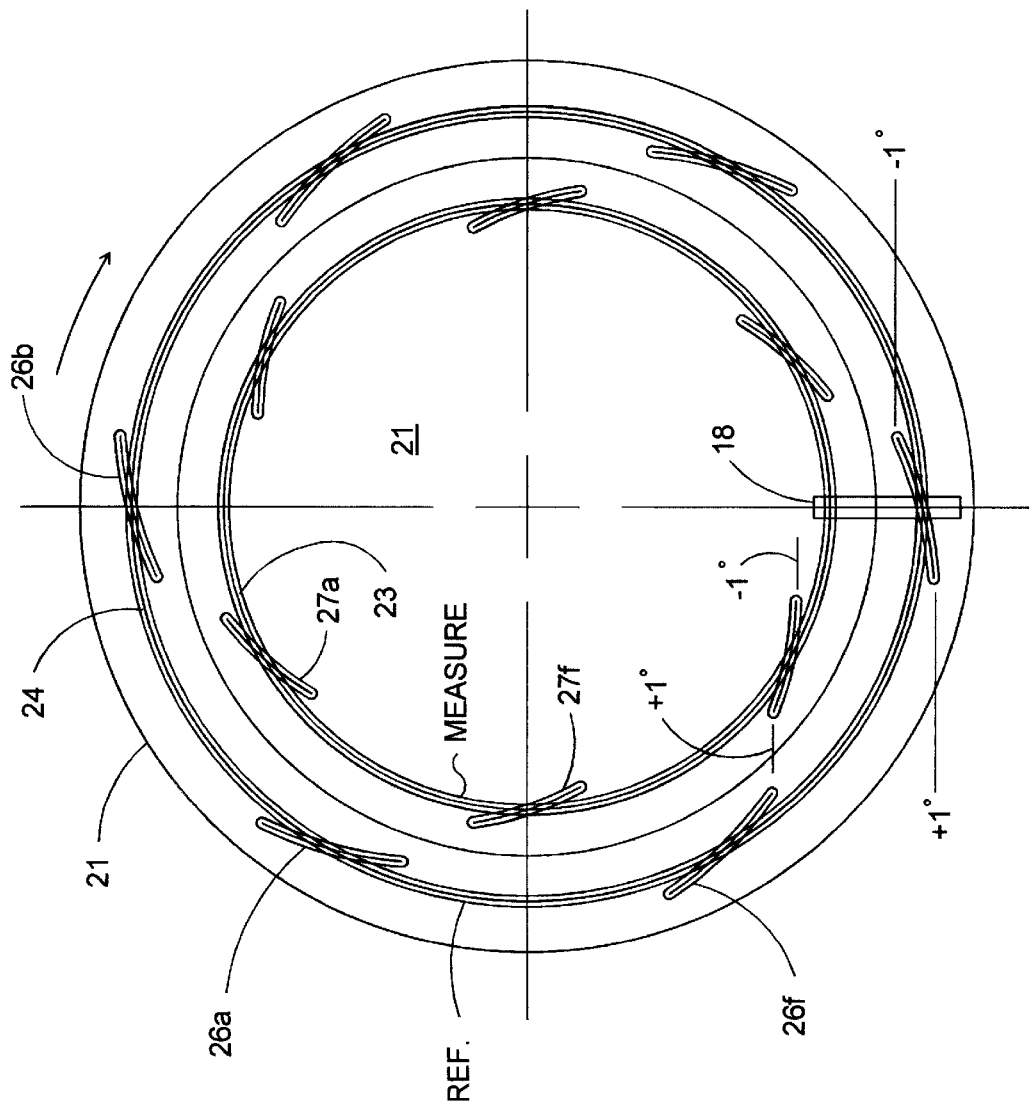
FIG. 2 is a plan view of a rotating disk taken along the line 2—2 of FIG. 1.

Finally to provide an oscillating light source there is a rotating disk 21 which is rotated by motor 22. Referring briefly to FIG. 2, the rotating disk 21 has an inner circular concentric track 23 and outer track 24 including the spiral segments which are in the form of six apertures 26a through 26f. The inner track 23 has staggered apertures 27a through 27f. These are staggered radially to allow only one light beam (reference or measurement) at a time to be received by detector 26. The illustration of how these apertures line up with the effective vertical line light source or slit provided by aperture 18 is illustrated by the apertures 26' and 27'. Since these apertures are spiral segments, they in effect oscillate between +1° and −1° as illustrated by the arrows in FIG. 3 so marked. Thus when the light passes through these crosswise moving apertures an oscillating light beam is formed both by the inner ring 23 and the outer ring 24.

Referring back to FIG. 1 these two separate light beams are indicated generally by the light rays 13 and they pass through a planoconvex lens 31 and through a source window 30 into the cavity 32 to provide an incident measuring beam or set of light rays 33 which is incident upon the surface of paper 11 and is reflected therefrom as shown by reflected beam 34 to impinge upon the detector 36. Then a direct beam 37, which is a reference light beam, which goes directly between the light source 14 and the detector 36. And there are of course an intermediate detector window 38, another planoconvex lens 39, angle reflector 41, a planoconvex lens 42 and finally the detector 36. Such detector is again in accordance with the above TAPPI standards to provide a CIE luminous efficiency function which has an effective wavelength of 572 nm.

The output signal of the detector 36 is illustrated in FIG. 4A. It has a first part shown at 46 which is a measurement signal produced by the incident light beam 33 and reflected light beam 34 and then both earlier and later in time a reference signal 47 which is produced by the direct beam 37 between the light source 14 and the detector 36. Details of the processing of this signal will be discussed below. But one of the advantages of the present invention is that because of the oscillating light source produced by the spiral segments 27a through 27f (see FIG. 2), compensation or immunity to movement of the paper sheet by tilting or waves is provided.

Figure 5:
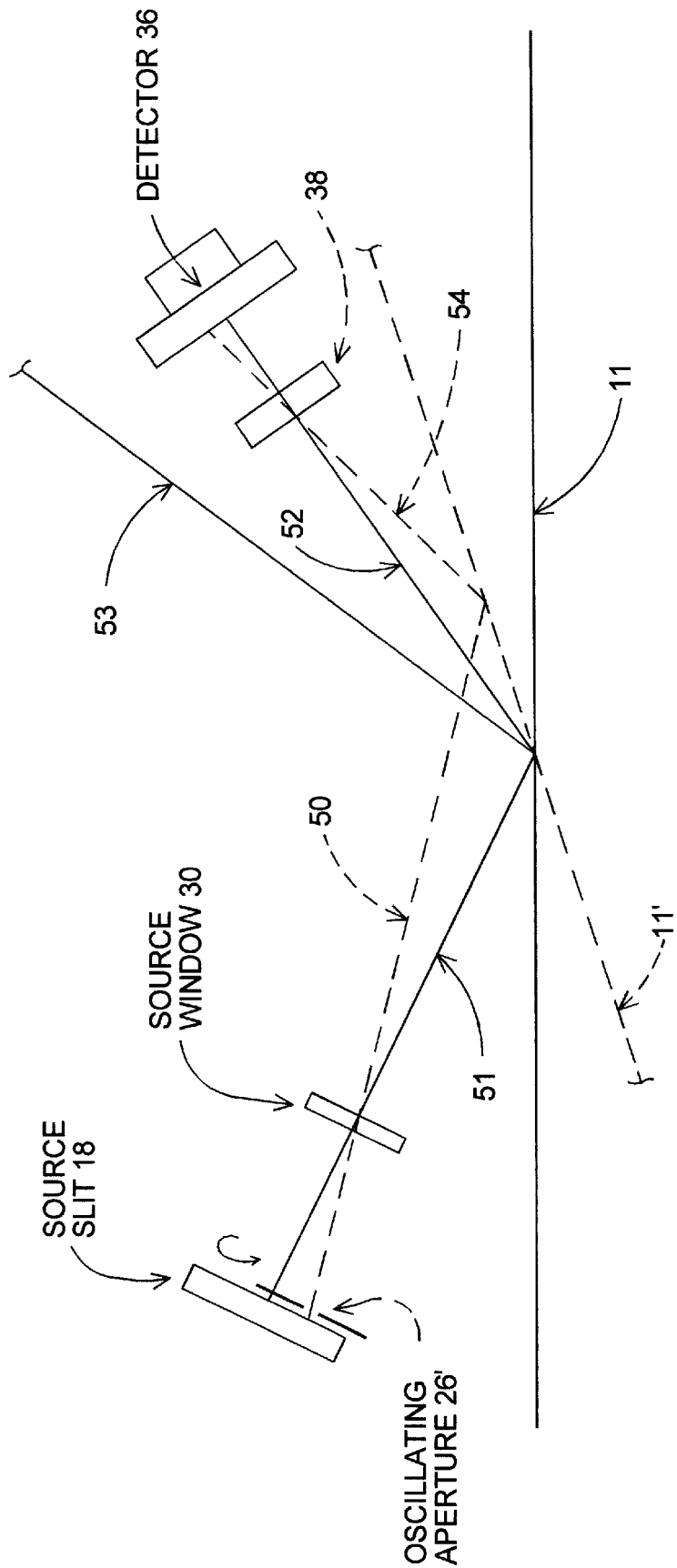
FIG. 5 is an illustration of various optical beam paths useful in understanding the invention as they are reflected from a paper sheet which may be either level or tilted.

FIG. 5 illustrates a nominally flat sheet 11 and then a tilted sheet 11' where the incident light beam is generally shown at 33. In the normal case light ray 51 impinges on the paper sheet 11 at, for example, a 15° angle in relation to the sheet, and then the reflected ray 52 goes toward the detector at the same angle. However, if the sheet tilts, as shown at 11', that beam now becomes the light ray 53 and misses the detector. However, because of the oscillation of the beam by oscillating aperture 27' (see FIG. 3) which changes the effective angle at which it hits the sheet, and also the location, the beam 50 will impinge upon the tilted sheet 11' at perhaps a relatively earlier or later point in time but will produce the reflected ray 54 which will be detected by the detector window 55. A vertical shift of the sheet (see FIG. 7) is compensated for in the same manner to ensure the light ray hits the detector.

Thus, in partial summary, the light source provides a crosswise moving slit across a fixed line source varying the angle of the beam to provide both a straight through path to provide both a reference and measurement beam with the same light source and detector beam. Secondly, the same crosswise moving slit provides for the measurement beam due to the oscillation provided by the spiral as indicated in FIG. 3, immunity or compensation for tilting or shifting paper. Of course, in the case of the reference beam, an oscillation is not absolutely necessary but if used, the required tolerances for the reference beam are relaxed.

Referring to FIG. 2 it is believed that the segments or fragmental spirals are the most efficient for producing both the measurement and reference beam paths and providing an oscillating movement. But alternatives such as oscillating slits 26, 27, driven, for example, by a separate driving unit or a tuning fork could also be used. And, of course, rather than the segmented slits as in FIG. 2, a continuous spiral would work but reduce the sampling rate by perhaps an order of magnitude.

Figure 6:
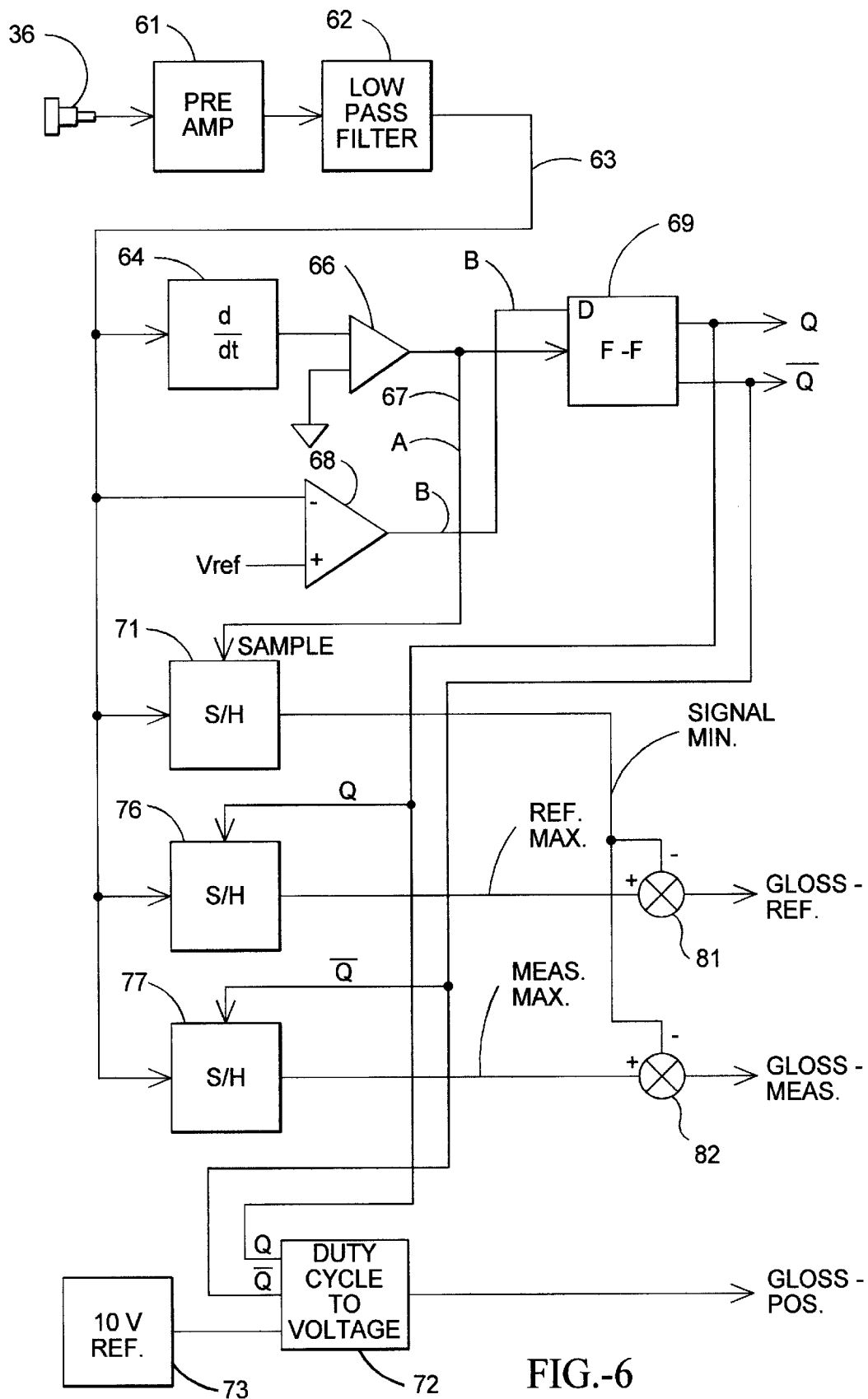
FIG. 6 is an electrical block diagram showing how signals are processed from the detector of the present invention.

The processing of the electrical signals from detector 36 are illustrated both in FIG. 6 and by the waveforms of FIG. 4. From a broad standpoint, all that needs to be done is that the peaks of the measurement and reference signals must be sensed, background noise subtracted out (indicated as signal minimum in FIG. 4A) and then the ratio taken to provide a signal directly proportional to gloss.

Referring now to the circuit of FIG. 6 in conjunction with FIG. 4, the output of detector 36 is connected to the preamplifier 61 which drives the low pass filter 62 which has a signal output on line 63 which is that illustrated in FIG. 4A. A derivative of the signal output is taken at 64 (FIG. 4B) and then fed through a comparator 66 to provide on the line 67 the A output indicated in FIG. 4D. Thus the differentiation finds the peaks of the signals 46, 47 and these are the trailing edges of the waveforms A of FIG. 4D. The leading edges are generated by the signal minimum. Another comparator 68 compares with a voltage reference, Vref, (FIG. 4A) to provide the waveform B illustrated in FIG. 4C. In other words, the reference signal is distinguished from the measured signal because of its much higher amplitude which, of course, is true because of the direct line between light source and detector. .A "D" type flip-flop 69 receives both the A and B signals as indicated and produces on its Q and Q bar outputs the signals shown in FIGS. 4E and 4F.

To provide an analog measurement of signal minimum, as indicated in FIG. 4A, there is an analog sample and hold (S/H) unit 71 with the A output on line 67 sampling the signal line 63. The two other S/H units 76 and 77 are driven respectively by the Q and Q bar signals (see FIGS. 4E and 4F) to provide the reference max signal and a measured max signal which are also indicated in FIG. 4A.

Signal minimum, which is background noise, is subtracted via the units 81 and 82 to provide inputs to the gloss computing unit 83 (see FIG. 9) of gloss-reference and gloss-measurement signals. The magnitude of gloss-meas. is related of course to gloss and the gloss-ref. signal is a standardization or calibration signal. In the computing unit 83 (FIG. 9) gloss (without being corrected for parallel paper shift to be discussed below) is a ratio of gloss-measurement and gloss-reference times a calibration factor A; namely, A(Meas./Ref.). The calibration is partially determined in the factory setup of the present unit by utilizing the black glass standard used by TAPPI. Then, of course, it depends on the various optical characteristics of the specific sensor unit dirt build up, drift, etc.

Figure 8:
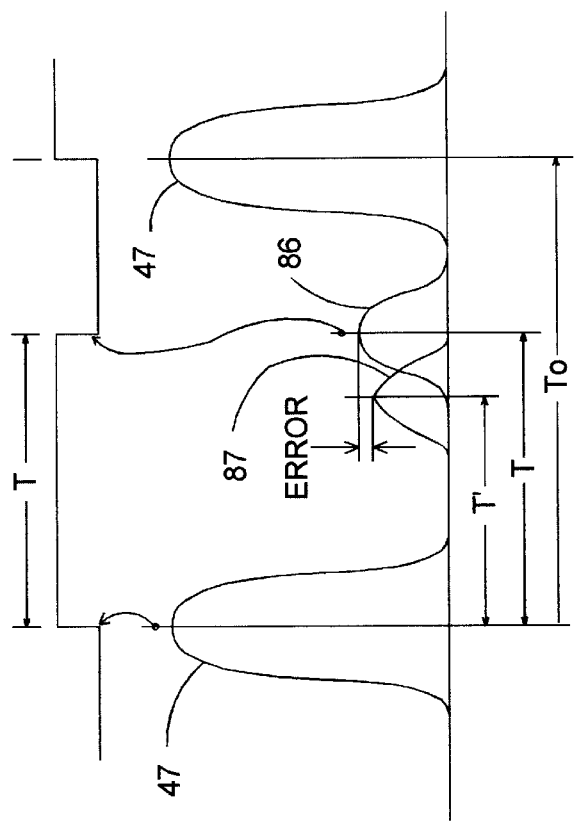
FIG. 8 shows waveforms similar to FIG. 4A but illustrating the effect of a parallel shift.
Figure 7:
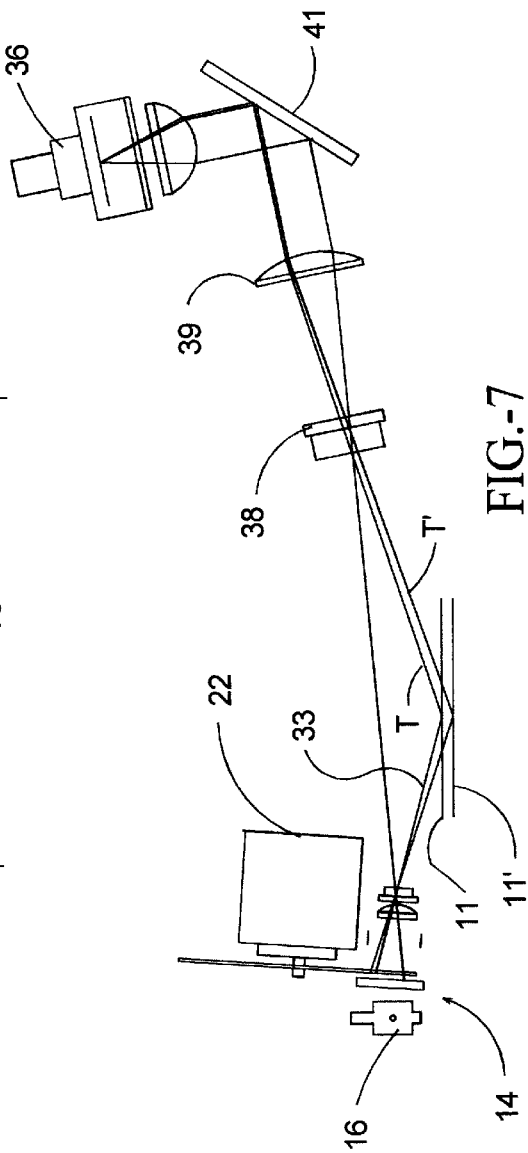
FIG. 7 is similar to FIG. 1 illustrating parallel shift of the paper sheet.

However, in addition to compensating for the tilting of the moving paper sheet, a parallel or vertical shift of a sheet should be accommodated in the paper making process. When high gloss paper is being produced, the air bearing supports for the paper cannot control the level of the paper too severely or otherwise undesirable marking of the high gloss paper results. Referring to FIG. 7 this parallel shift is illustrated where the desired level or location of the paper is shown at level 11' but actually the paper is at the level 11. This causes a change of the angle of reflection, as well as incidence of the light beam. But without any additional correction the oscillating angle light source of the present invention still accommodates this change of angle so that a reflected beam is still received at the intermediate detector window 38. But, as illustrated in FIG. 8, the received measured detected light waveform 86 is shifted in time designated the time interval T from the reference signal 47 compared to the nominal standardized 15° signal 87 which has been designated as having a time interval T'. This is a theoretical time interval for the reflected light detected at the standardized 15° TAPPI angle. The parallel shift shown in FIG. 7 from 11' to 11 causes this change of time which is directly proportional to angle of incidence and reflection. Thus in accordance with the present invention by comparing the actual measured time interval T to the theoretical time interval T' for the standardized angle of 15°, a corrected gloss measurement (corrected for parallel shift) may be obtained. Still referring to the comparison between the measured waveform 86 and a theoretical waveform 87, because of the shallower angle produced by the paper sheet being shifted to the position shown at 11 in FIG. 7, according to Fresnel's law, such shallower angle produces a greater reflection. Thus, the amplitude of waveform 86 is higher than the standard waveform 87 and the resulting measurement error is illustrated. This error has been found to be about eight percent per degree of angle change.

To summarize, the deviation of the effective incident angle of the beam to the moving surface from a theoretical TAPPI angle is proportional to the change in time interval. As will be discussed below, because of Fresnel's law, this is non-linear.

Figure 9:
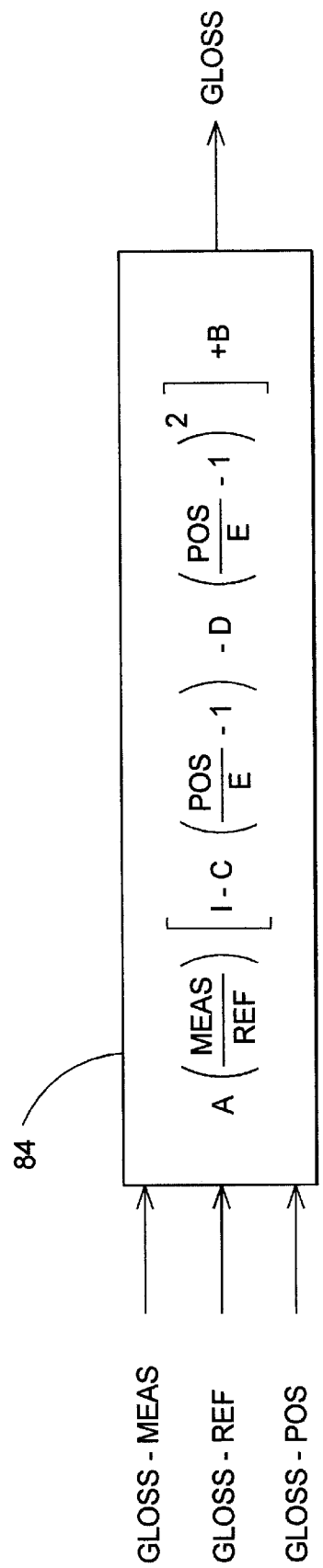
FIG. 9 is a block diagram showing how signals are processed.

As discussed above, a suitable gloss measurement is provided even if no correction for a parallel shift is made by taking a ratio as illustrated in FIGS. 6 and 9 of the gloss-ref. and gloss-meas. outputs. However to correct for parallel shifts, as illustrated in FIG. 6 a duty cycle to voltage unit 72 is driven by the Q and Q-bar inputs and also a 10 volt reference unit 73 (10 volts is merely chosen for convenience; this could be any arbitrary voltage). The output is in a measurement termed gloss-pos which is also connected as shown in FIG. 9 to the computational unit 83. It is clear from the equation or algorithm shown there that "pos" is a correction factor which if not needed drops out and then the gloss measurement is dependent only on the ratio of the remaining measurements.

Figure 6A:
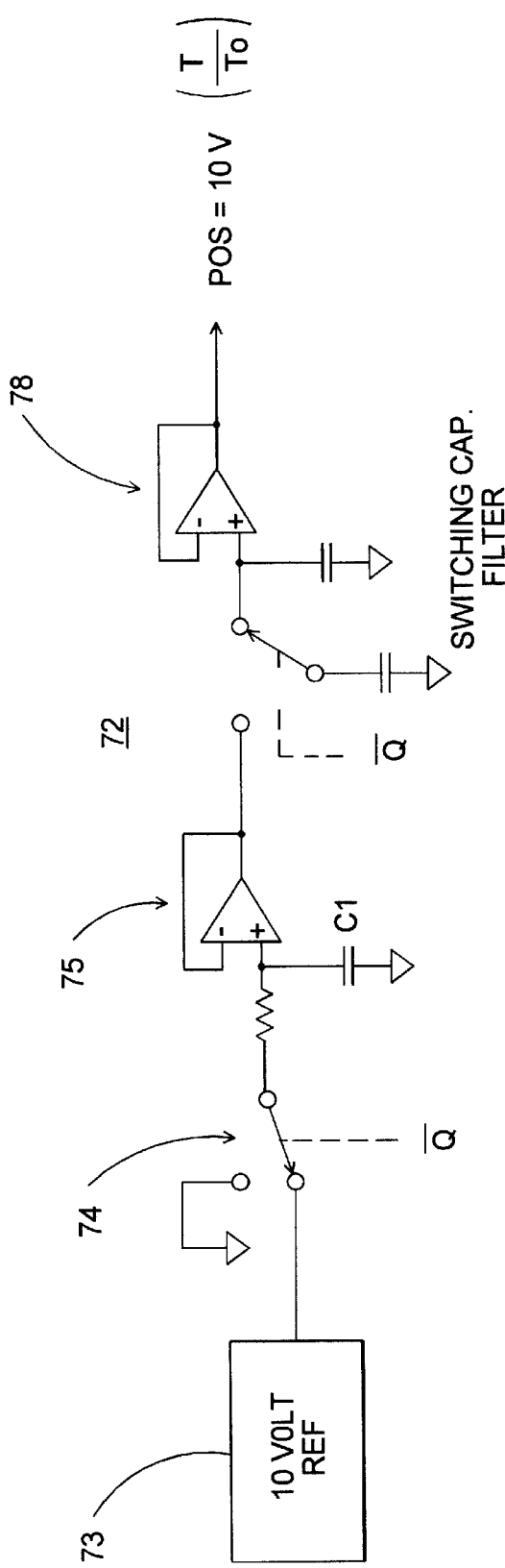
FIG. 6A shows a block of FIG. 6 in detail.

FIG. 6A illustrates the circuitry for the duty cycle to voltage conversion unit 72. Here the 10 volt reference unit 73 is connected to one terminal of a switch 74 which is driven by the Q bar output between the reference unit and ground. An operational amplifier 75 with an associated capacitor C1 is charged toward the 10 volt reference voltage as long as switch 74 is in the position illustrated. Thus the charge on capacitor C1 is directly proportional to the duty cycle having a time interval T of the wave form 86 as illustrated in FIG. 8. This voltage on C1 is captured by the switching capacitor filter 78 whose switch is driven by Q. Thus the output of the duty cycle to voltage unit 72 is 10 volts times the ratio of T and $T_O$. This voltage is then coupled to the computational unit 83 in FIG. 9 and the correction made as shown by the algorithm to provide a corrected gloss output.

Specifically as illustrated the gloss sensor algorithm calculates the gloss from the following three sensor outputs:

GLOSS-MEAS
GLOSS-REF
GLOSS-POS $$Gloss = A*(I1/I2)*\{1-C*(I3/E-1)-D*(I3/E-1)^2\}+B,$$

where:
I1=GLOSS-MEAS
I2=GLOSS-REF
I3=GLOSS-POS
A=aplus.sensor.gloss.coeA
B=aplus.sensor.gloss.coeB
C=aplus.sensor.gloss.coeC
D=aplus.sensor.gloss.coeD
E=aplus.sensor.gloss.coeE Default value for A is 100, B, C, and D will default to zero and E is a scaling factor with a default value of 100,000. I3/E is made equal to one when the TAPPI angle of 15° is present. B is a calibration constant which varies the final gloss output by less than ±2%.

The foregoing is accomplished in a standard computer language such as C++. The above equation is, of course, exactly equivalent to that shown in FIG. 9. The squared term provides the non-linearity of Fresnel's law.

With regard to the relative change in time illustrated in FIG. 8 between the actually measured signal 86 and the theoretical signal 87, whether this is a "leading" or "lagging" function is dependent on the direction of rotation of the rotating spirals illustrated in FIG. 2.

Where the erroneous angle is due to tilt of the paper only the above correction is not believed to be as effective. But most flutter is mainly a parallel shift.

Thus in summary an improved gloss sensor has been provided where because of the separate reference beam which uses the same light source detector as the measuring beam, standardization and calibration is easily accomplished. Then this same technique for producing the reference beam, that is the oscillating slit on the light source also compensates for a tilted or wavy paper surface and also parallel shift.

What is claimed is:

1. A gloss sensor for determining the gloss of a moving surface comprising:

light source means for emitting an incident light beam onto the moving surface at oscillating angles and causing a light beam to be reflected from said surface;

a light detector positioned to detect the reflected light;

said light source means providing an emission of light at said oscillating angles substantially near such incident angle whereby any tilt or shift of said moving surface which would otherwise cause said reflective light to miss said detector is compensated for;

means for sensing the magnitude of detected light to determine a gloss value of such surface;

and means for scanning across said moving sheet and for carrying and positioning said light source means and said light detector in close proximity to said moving sheet.

2. A gloss sensor as in claim 1 where said light source means is a fixed line light source including a crosswise oscillating aperture on said line to provide said oscillating angles.

3. A gloss sensor as in claim 2 where said fixed line light source means includes a lamp juxtaposed to a diffuser sheet which in turn is juxtaposed to a rectangular window to provide said fixed line.

4. A gloss sensor as in claim 2 where said oscillating aperture is formed by an effective rotating spiral.

5. A gloss sensor as in claim 4 said light source means providing a reference beam aimed directly at said detector without said reflection in addition to said incident beam and where said rotating spiral includes an outer spiral set for said reference beam and an inner spiral set for said incident beam.

6. A gloss sensor as in claim 5 where said spiral sets alternate between inner and outer sets so that the common detector alternately receives an incident beam and a reference beam.

7. A gloss sensor as in claim 5 where said reference beam provides a reference signal at the output of said detector and said incident beam provides a measurement signal at the output of said detector whose intensity is related to gloss and including means for electronically processing said signals from said detector including sensing the peaks of both said measured signal and said reference signal and then taking their ratio to provide a signal directly proportional to gloss.

8. A gloss sensor as in claim 2 where said crosswise aperture includes a rotating disk having two concentric circular tracks each with apertures.

9. A gloss sensor as in claim 8 where such apertures are staggered to allow only one beam at a time to be received by said detector.

10. A gloss sensor as in claim 3 where said diffuser sheet is composed of a tetrafluoroethylene resin with a thickness of 20–30 microns.

11. A gloss sensor as in claim 8 where such apertures of at least one track are fragmented portions of a spiral to provide a said incident light beam having an oscillating angle.

12. A gloss sensor as in claim 1 where said light source means includes a single lamp for providing said incident beam and where said angle of incidence is desired to be a standard fixed angle including means for compensating for parallel shifts of said moving surface which cause a deviation from said standard fixed angle including means for measuring the time interval for said reflected light to be detected from a reference time and means for comparing such time interval to the theoretical time interval for reflected light to be detected which has no such deviation for correcting the error in gloss value caused by said deviation.

13. A gloss sensor as in claim 12 where said means for measuring said detection time interval includes means for measuring the duty cycle of a pulse generated by said reflected light.

14. A method for measuring the gloss of a moving surface comprising the following steps;

emitting an incident beam of light along an optical axis at oscillating angles to such surface to cause a reflective beam of light to be reflected from the surface;

detecting the intensity of said reflected light;

said oscillating of said incident beam of light compensating for any tilt or shift of said moving surface which would otherwise cause said reflected light to miss said detector;

determining the gloss of the surface based upon the magnitude of said detected intensity;

and independently from said oscillating, scanning said light source across said moving paper.

* * * * *